US012752028B2

(12) United States Patent
Riedel et al.

(10) Patent No.: US 12,752,028 B2
(45) Date of Patent: Oct. 6, 2026

(54) DEVICE FOR DECONTAMINATING OBJECTS

(71) Applicant: CLARANOR, Avignon (FR)

(72) Inventors: Christophe Riedel, Avignon (FR); Pierre Lalubin, Graveson (FR); Julien Dubois, Rochefort du Gard (FR)

(73) Assignee: CLARANOR, Avignon (FR)

( * ) Notice: Subject to any disclaimer, the term of this patent is extended or adjusted under 35 U.S.C. 154(b) by 484 days.

(21) Appl. No.: 18/004,569

(22) PCT Filed: Jul. 2, 2021

(86) PCT No.: PCT/EP2021/068314

§ 371 (c)(1),
(2) Date: Jan. 6, 2023

(87) PCT Pub. No.: WO2022/008369

PCT Pub. Date: Jan. 13, 2022

(65) Prior Publication Data

US 2023/0241274 A1 Aug. 3, 2023

(30) Foreign Application Priority Data

Jul. 8, 2020 (FR) ....................................... 2007209

(51) Int. Cl.

| | |
|---|---|
| ***A61L 2/26*** | (2006.01) |
| ***A61L 2/10*** | (2026.01) |
| ***A61L 2/24*** | (2006.01) |

(52) U.S. Cl.

CPC *A61L 2/26* (2013.01); *A61L 2/10* (2013.01); *A61L 2/24* (2013.01); *A61L 2202/11* (2013.01);

(Continued)

(58) Field of Classification Search

CPC ..... A61L 2/26; A61L 2/10; A61L 2/24; A61L 2202/11; A61L 2202/14; A61L 2202/16
See application file for complete search history.

(56) References Cited

U.S. PATENT DOCUMENTS

| | | | |
|---|---|---|---|
| 9,809,435 | B2 | 11/2017 | Houde |
| 2012/0211645 | A1 | 8/2012 | Tullo et al. |

(Continued)

FOREIGN PATENT DOCUMENTS

| | | | |
|---|---|---|---|
| CN | 111134029 A * | 5/2020 | |
| FR | 2990135 A1 | 11/2013 | |

(Continued)

OTHER PUBLICATIONS

English Translation of JP2014528802A (Year: 2014).*

(Continued)

*Primary Examiner* — David E Smith
*Assistant Examiner* — Laura Eloise Tandy
(74) *Attorney, Agent, or Firm* — Greer, Burns & Crain, Ltd

(57) ABSTRACT

A device for decontaminating stoppers, including a decontamination zone in which the stoppers move, at least one source emitting decontaminating light radiation into the decontamination zone, and is for positioning the stoppers in the decontamination zone and includes at least two elements for guiding the stoppers, and a cooling circuit for cooling the decontamination zone, in which the cooling circuit is integrated into the positioning device. The device includes at least two elements for guiding the stoppers including two lateral rails each including a zone of contact with at least one stopper and at least one reflective zone which is contiguous with the contact zone and in which it is able to reflect the light radiation onto the at least one stopper.

18 Claims, 4 Drawing Sheets

(52) U.S. Cl.
CPC ....... *A61L 2202/14* (2013.01); *A61L 2202/16* (2013.01)

(56) References Cited

U.S. PATENT DOCUMENTS

| | | | | |
|---|---|---|---|---|
| 2012/0248332 | A1* | 10/2012 | Kreitenberg | A63B 47/04 250/455.11 |
| 2012/0273693 | A1* | 11/2012 | Houde | B67B 3/003 250/453.11 |
| 2016/0101201 | A1* | 4/2016 | Franc | B67B 3/003 422/24 |
| 2017/0203869 | A1* | 7/2017 | Lucani | B65B 59/003 |

FOREIGN PATENT DOCUMENTS

| | | | | |
|---|---|---|---|---|
| JP | 2005080809 | A | * | 3/2005 |
| JP | 2014528802 | A | * | 10/2014 |
| WO | 2010044748 | A1 | | 4/2010 |

OTHER PUBLICATIONS

English Translation of CN111134029A from Espacenet (Year: 2020).*
Espacenet English Translation of JP 2005080809 A, Kikuchi (Year: 2005).*
French Search Report received for Application No. 2007209, dated Apr. 7, 2021.
International Search Report and Written Opinion received for PCT/EP2021/068314, mailed Sep. 20, 2021.

* cited by examiner

DEVICE FOR DECONTAMINATING OBJECTS

BACKGROUND

The invention relates to a device making it possible to decontaminate objects, and in particular closures or any other object (of wrapping or packaging, or not) that can be conveyed in a line. The device is designed to be utilized in an installation in which the closures are moved from one treatment station to another.

The invention has a particular application in decontaminating closures, but it must be understood that it could also have an application in decontaminating other objects, such as containers conveyed one after the other in a tunnel or other corridor in which their movement is ensured.

The objects are in particular objects having an outer part and an inner part, where the inner part can be a concave part.

The decontamination of closures is essential in installations for packaging products, in particular food products, in particular to prevent germs that may be present on the closures from coming into contact with the product to be packaged.

A high-speed device and appliance which use pulsed light to decontaminate the interior of the closures are known from document FR 2 951 949. The device includes a decontamination area in which the closures move between a decontamination area entrance and a decontamination area exit. It also includes at least one source for emitting a light radiation into the decontamination area, the light radiation being suitable for decontaminating said closures moving in said area, a device for positioning the closures in the decontamination area, to position the closures in a predetermined arrangement, including at least two elements for guiding said closures and a circuit for cooling the decontamination area, to keep the decontamination area at a temperature below a predetermined temperature when the decontamination area receives said light radiation, said cooling circuit being integrated into said positioning device.

By “light radiation” will be meant an emission of visible or invisible light, comprising in particular ultraviolet radiation, visible radiation and infrared radiation.

By “decontamination” will be meant the action that tends to eliminate germs or other pathogenic agents capable of spoiling a food product or of causing an illness in humans or animals.

The device described in the above-mentioned document has the characteristic of only decontaminating the interior of the closures.

SUMMARY

The invention aims to decontaminate the whole object, i.e. the interior of an object but also the exterior thereof. In fact, the exterior treatment of the closures is necessary, for example, for the packaging of very sensitive products, in order to prevent the germs that are present on the exterior of the closures from entering a packaging area and leading to contamination of the product.

For this purpose, the invention relates to a device for decontaminating objects, including:

- a decontamination area in which the objects move by means of gravity between a decontamination area entrance and a decontamination area exit,

- at least one source for emitting a light radiation into the decontamination area, said light radiation being suitable for decontaminating said objects moving in said area,
- a device for positioning the objects in said decontamination area, to position the objects in a predetermined arrangement, including at least two elements for guiding said objects.

The device according to the invention is notable in that said at least two elements for guiding said objects include at least one lateral rail comprising a contact area with at least one object and at least one reflective area which is contiguous with said contact area and which is suitable for reflecting said light radiation onto said at least one object, said reflective area being at least partially constituted by a face of said at least one lateral guide rail.

Realized in this way, the rail makes it possible to reflect the decontaminating radiation onto the side wall of the closures, which allows it to contribute to the decontamination of the exterior of the closures.

It should be noted that by giving the rail a decontamination function, simply passing the object over the rail simultaneously ensures that it is decontaminated, the radiation being emitted as the object passes over the lateral rail.

Realizing a rail with a reflective face contributes to limiting the bulk of the device and the fact that the reflective face is on a lateral rail makes it possible to reflect the decontaminating radiation more since the decontaminating radiation easily arrives on the lateral rail if the emission source is placed above or below the decontamination area.

Thus, the reflective area is located in a plane lateral to the source for emitting to the decontaminating radiation.

In order to make this reflection possible, as well as an efficient decontamination, the contact area must be as small as possible: this is why the contact area between the object and the rail is limited to a contact point or a contact line. The reflective area of the rail, which is contiguous with the contact area, is oriented according to a plane which forms an angle with the lateral surface of the object coming into contact with the rail.

Thus, providing that the rail has a part which constitutes a reflective area imposes a profile shape which is distinctive on the rail. As will be seen hereinafter, the profile of the rail according to an advantageous embodiment is V-shaped, the contact area being realized by the point of the V so that the contact is limited to a point or a line between the object and the rail. The two faces of the rail forming the V, which are contiguous with the contact area, can be two reflective areas.

According to an embodiment variant, only one of the two faces of the rail forming the V could be reflective.

According to advantageous embodiments, the device according to the invention can include the following characteristics, separately or in combination:

The contact area of said at least one lateral rail can be situated in at least two different locations in said decontamination area, including a first location in said decontamination area in which the contact area of said at least one rail touches at least one of said objects at a first contact point, line or surface but not at a second contact point, line or surface and a second location in said decontamination area in which the contact area of said at least one rail touches the same object at the second contact point, line or surface but not at the first contact point, line or surface, said second contact point, line or surface on said object being different from said first contact point, line or surface.

Furthermore, the device can include a control device of the source for emitting the light radiation arranged and/or programmed to emit said light radiation, preferably in the form of a plurality of flashes of light, in the first location in said decontamination area then in the second location in said decontamination area, the flash of light emitted in said first location being distinct from the flash of light emitted in the second location.

Still furthermore, said at least one lateral guide rail can have a V-shaped profile, comprising two contiguous faces suitable for reflecting said light radiation and constituting two reflective areas, the two faces extending on either side of a ridge constituting said contact area of said at least one lateral rail with said at least one object moving in said decontamination area, said contact area being linear and straight.

According to an advantageous embodiment presented hereinafter, it can be provided that said at least one lateral rail is made of metal.

Advantageously, said at least one reflective area can have a roughness of less than 0.2 μm.

According to an embodiment, the device can include a circuit for cooling the decontamination area, to keep said positioning device at a temperature below a predetermined temperature when the decontamination area receives said light radiation, said cooling circuit being integrated into said positioning device at least partially in said at least one lateral rail.

According to another advantageous embodiment variant, said guide elements can include at least one plate, said plate being positioned above or below the objects and suitable for being passed through by said light radiation emitted by said at least one source for emitting light radiation.

Furthermore, according to an embodiment which will be presented hereinafter, the device can include a first source for emitting a first light radiation and a second source for emitting a second light radiation, and in that the guide elements include two plates suitable for allowing a light radiation to pass through making it possible to decontaminate said objects, one of the two plates being positioned above said objects and suitable for being passed through by said first light radiation emitted by said first source of light radiation, for the decontamination of the exterior of said objects, and the other plate being positioned below said objects and suitable for being passed through by said second light radiation emitted by said second source of light radiation, for the decontamination of the interior and at least partially the exterior of said objects. Said at least one source for emitting light radiation can be a source for emitting pulsed light.

Advantageously, said at least one source for emitting light radiation can be combined with a reflector, to focus said light radiation emitted by said at least one source onto the objects in said decontamination area.

In the context of a particularly advantageous embodiment, it can be provided that the light radiation emitted by said at least one emission source is an ultraviolet radiation the wavelength of which is preferably comprised substantially between 200 and 300 nm.

The device can include a conduit which extends between the entrance and the exit of the decontamination area, said conduit including said at least one lateral rail on which the objects are at least partially guided and including at least a first wall having at least a first window receiving a first plate, suitable for allowing a light radiation to pass through making it possible to decontaminate said objects, said first window extending substantially from a first end of the conduit to substantially a second end of the conduit under said source for emitting light radiation, said conduit being leakproof to allow it to be cleaned.

Furthermore, the conduit can include a second wall, opposite said first wall, said second wall having at least a second window receiving a second plate suitable for allowing a light radiation to pass through making it possible to decontaminate said objects, said second window extending substantially from a first end of the conduit to substantially a second end of the conduit under a second source for emitting light radiation.

According to an embodiment, the device can include a first set of two guide rails which extends at a first height and over a first length of decontamination area between said entrance and said exit of the decontamination area, and a second set of two guide rails which extends at a second height, different from said first height, and over a second length of decontamination area, said second set of guide rails being consecutive and contiguous with the first set of guide rails so that the objects moving in said decontamination area are guided first by said first set of rails then by the second set of guide rails and so that a first contact area on the objects moving between the guide rails of the first set and corresponding to the contact area of the first set of guide rails is decontaminated by the light radiation when the objects move between the guide rails of the second set of guide rails.

According to yet another embodiment, the device can include two lateral rails, each extending in a curved (non-linear) direction, to generate a lateral displacement of the objects moving in said decontamination area.

According to yet another embodiment according to the invention, said at least one lateral rail can extend in a curved (non-linear) direction and generating a linear and straight displacement of the objects in said decontamination area without lateral displacement.

The invention also relates to a method for decontaminating objects utilizing a device as defined above, said method ensuring:

- the movement by means of gravity of objects in the decontamination area between said entrance of said decontamination area and said exit of said decontamination area, said objects being guided in a predetermined position by at least two guide elements of a positioning device,
- the decontamination of said objects moving in said area by emitting a light radiation into the decontamination area, said method being notable in that
- the decontamination of said objects is carried out at least partially by the reflection of said light radiation onto said at least one object on at least one reflective area of at least one lateral rail which said at least two guide elements include, and in that
- the movement of said objects is carried out by contact of said objects on a contact area of said at least one lateral rail, said contact area being contiguous with said reflective area of said at least one lateral rail, said reflective area being constituted by a face of said at least one lateral rail.

In other words, the contact area and the reflective area are created by two different parts of a lateral guide rail and they are positioned next to one another.

BRIEF DESCRIPTION OF THE DRAWINGS

Other advantages and characteristics of the invention will become apparent on examining the detailed description of an implementation which is in no way limitative, and from the attached drawings, in which.

DETAILED DESCRIPTION

In the description which follows, the terms "above", "below", "right", "left", "high", "low", etc. refer to the arrangement of the elements represented in the figures and make it possible to identify the elements to which the description refers more clearly. It must be understood that these terms are not limitations of the invention.

It should be noted that the embodiments described below could vary without exceeding the scope of the invention. These embodiments are given by way of illustration and are not intended to limit the scope of the invention.

Figure 1:
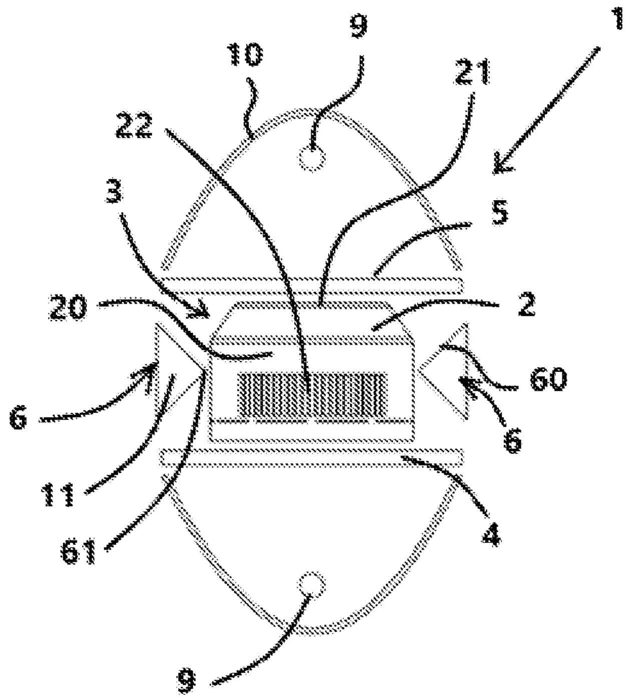
FIG. 1 is a diagrammatic cross-sectional view of a device according to a first embodiment of the invention.
Figure 2:
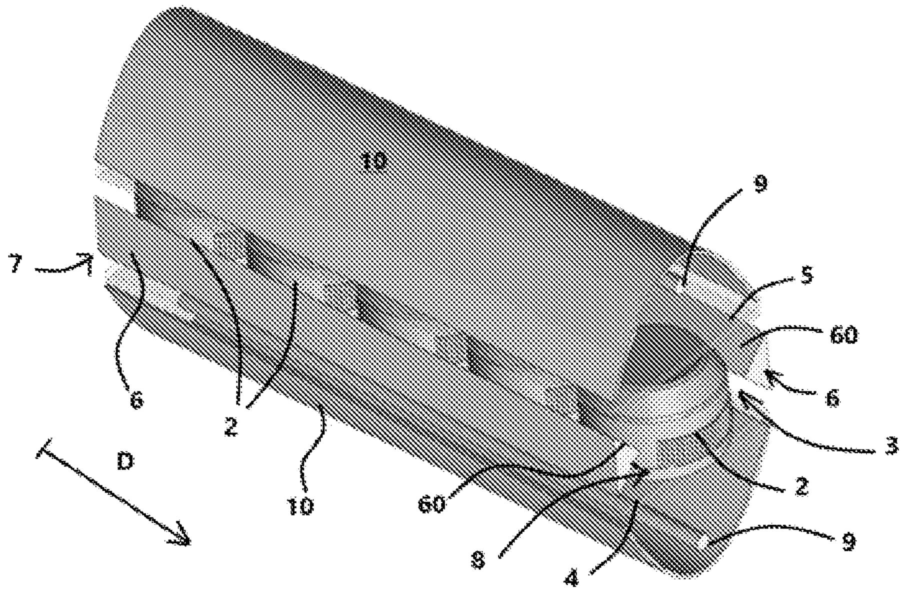
FIG. 2 is a perspective view of the device shown in FIG. 1.

FIGS. 1 and 2 refer to a first embodiment according to the invention.

A device 1 ensuring the decontamination of a closure 2 is observed.

In a conventional manner, the closure 2 has a lateral skirt 20, of substantially cylindrical shape, an uppermost wall 21 which closes the upper end of the closure. The lateral skirt 20 has, on its outer surface, one or more striated radial parts 22 and, on its inner surface, a thread allowing the closure to be screwed onto the neck of a container or an internal rim allowing the closure to be clipped onto a container neck.

The closure 2 is located in a decontamination area 3 of the device 1, the decontamination area 3 being delimited:

between a lower wall 4 and an upper wall 5, between which the closure 2 is positioned, and two lateral guide elements 6, between which the closure 2 is also positioned.

The lower 4 and upper 5 walls, as well as the lateral guide elements 6, extend between the ends of the decontamination area.

FIG. 2 also shows the device 1 and its decontamination area 3: several closures 2 are moving in the decontamination area 3 in the direction of the arrow D (from left to right) between a decontamination area entrance 7 and a decontamination area exit 8, the entrance 7 and the exit 8 being situated at the ends of the decontamination area 3. Thus, the lower 4 and upper 5 walls, as well as the lateral guide elements 6, extend between the entrance 7 and the exit 8 of the decontamination area 3.

The lower 4 and upper 5 walls are realized by transparent quartz plates, suitable for allowing a light radiation to pass through making it possible to decontaminate the closure or closures present between the two plates 4 and 5.

It must be understood that the quartz plates could be replaced with other plates allowing the transmission of a decontaminating radiation other than UV without exceeding the scope of the invention.

The two lateral guide elements 6 are lateral rails preferably made of stainless steel and, in the context of this example, having a triangular section. The advantage of making the rails from stainless steel is to allow them to be cleaned easily.

Each of the lateral rails has two contiguous faces 60 forming a V, which are suitable for reflecting a light radiation which would strike them.

The faces 60 thus constitute reflective areas of each of the lateral rails 6.

It is provided that the faces 60 of the guide rails 6 made of stainless steel are mirror-polished (having a roughness of less than 0.2 μm), which makes it possible in particular to reach a reflection coefficient of more than 50% in the ultraviolet.

It should be noted that the roughness of less than 0.2 μm makes the material compatible with constraints relating to hygiene, the absence of abrasion and cleaning which are usually required.

The reflection coefficient of the lateral rails 6 is at least 30% for ultraviolet radiation the wavelength of which is substantially 300 nm.

The two contiguous faces 60 meet along a ridge 61, against which the skirt 20 of the closure or closures 2 can rest: the ridge 61 thus constitutes a contact area with the closure or closures and this area is contiguous with at least one reflective area (in this case, in the context of this example, the contact area is contiguous with two reflective areas constituted by the faces 60, forming a V, of the rail 6).

It will be noted that the contact area between the closures 2 and the guide rails 6 is limited to a straight line, constituted by the ridge 61: the contact between the guide rails and the closures is thus limited to a point (the guide rail being tangential to the circular surface of the skirt 20 of the closure 2), thus leaving a large lateral part of the closures free to be exposed to the decontaminating radiation. The decontaminating radiation can in fact be reflected by the faces 60 of the rails and strike the skirt 20 of the closure or closures 2, thus making it possible to decontaminate the lateral part of the closure or closures 2.

Thus, realizing the rail with a reflective face that is contiguous with a contact area (with the object to be decontaminated) makes it necessary to realize the rail with a particular shape: it is thus noted that the face of the lateral rail which forms the reflective area is inscribed in a plane that is inclined with respect to the lateral wall of the object in contact with the rail in the contact area.

The lateral guide rails 6, as well as the quartz plates 4 and 5, contribute to the ordered sliding of the closures 2 in the decontamination area.

According to the invention, the device 1 includes at least one source 9 for emitting a light radiation, suitable for decontaminating the closures 2.

In the context of the example presented, the device 1 includes two sources 9 for emitting decontaminating light radiation, each source being positioned perpendicular to the transparent quartz plates 4 and 5 (i.e. above the quartz plate 5 and below the quartz plate 4).

Each of the sources 9, preferably, includes a lamp emitting in particular UV, being capable of emitting the UV light either in the form of flashes (for example xenon flash lamp) or continuously (called low- or medium-pressure UV lamp). The radiation emitted comprises in particular the wavelengths comprised between 200 and 400 nm, preferably between 200 and 300 nm.

The space surrounding each of the sources 9 (or lamps 9) is enclosed by a reflecting tunnel 10, having a substantially bell-shaped section, the tunnel 10 preferably being made of a reflective material, for example aluminium.

The wall constituting the reflecting tunnel 10 forms an enclosed space surrounding a lamp 9, the wall being curved and allowing the light radiation emitted by the lamp 9 also to be reflected in order to focus it towards the decontamination area 3, in which the closures 2 are moving, through the quartz plate 4 or 5, to decontaminate respectively either the interior of the closure 2 or the interior and the exterior of the closure 2.

The emission of decontaminating light radiation causes a rise in temperature which must be prevented so that the closures 2, which are moving in the device, are not deformed or impaired.

For this reason it is provided that the device according to the invention is equipped with a circuit 11 for cooling the decontamination area 3 in which the light radiation is emitted.

It is advantageously provided to keep the decontamination area at a temperature below a temperature of 50° C., or substantially below 50° C. (predetermined temperature which ensures that the closure is not deformed or deformable on contact with the rails, the rails being the elements which increase in temperature and which cause the temperature in the decontamination area to increase).

In the context of this example, it is provided to integrate the cooling circuit 11 into the guide rails 6: in particular, the rails 6 are provided hollow and a channel is provided inside each of the guide rails 6, to circulate a cooling fluid therein, for example deionized water.

The guide rails 6 are thus cooled and their design in stainless steel (or other) allows them not to be impaired by the cooling fluid.

Figure 3:
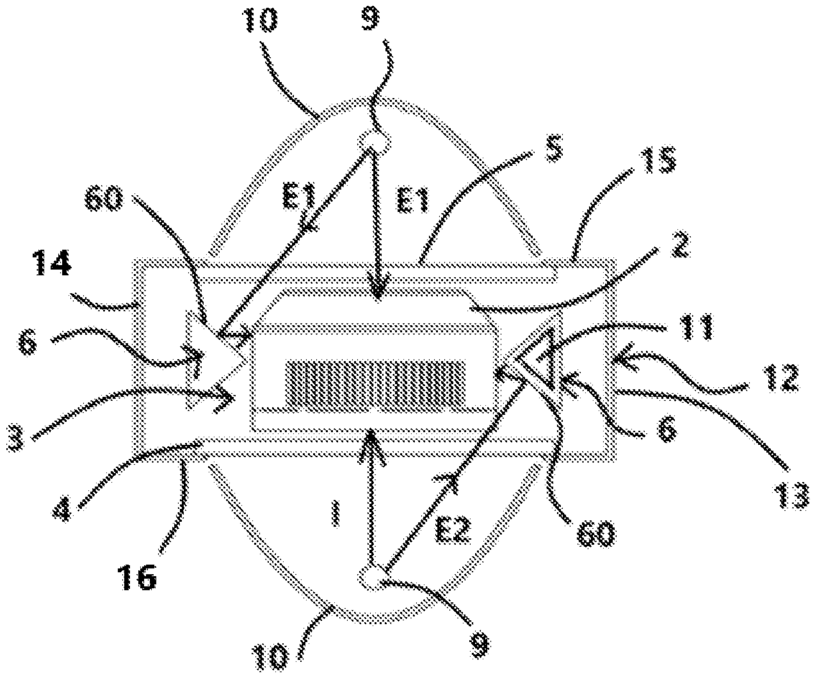
FIG. 3 is a diagrammatic cross-sectional view of a device according to a second embodiment of the invention.
Figure 4:
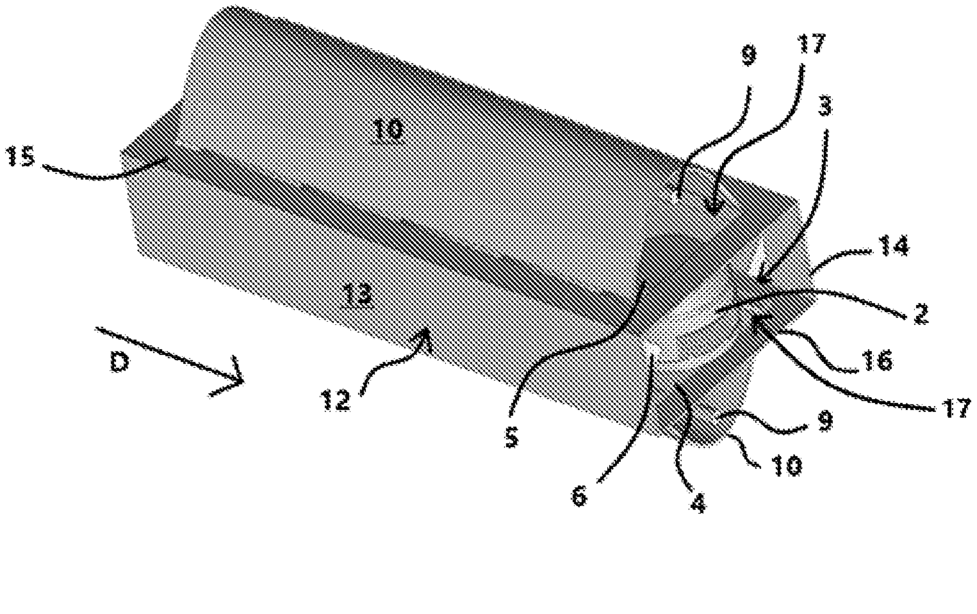
FIG. 4 is a perspective view of the device shown in FIG. 3.

Another embodiment example of a device according to the invention is illustrated in FIGS. 3 and 4.

In the context of this second example, the device includes, like the first device shown in FIGS. 1 and 2, a first source for emitting a first light radiation (first lamp 9 for emitting UV radiation, positioned in the upper part of the device) and a second source for emitting a second light radiation (second lamp 9 for emitting UV radiation, positioned in the lower part of the device).

The decontamination area 3 is situated substantially between the two sources for emitting light radiation.

The device also includes guide elements, including two lateral guide rails 6 identical to those of the embodiment described previously and illustrated in FIGS. 1 and 2, as well as two parallel quartz plates 4 and 5 (respectively lower and upper) between which the closures 2 are guided.

Among the two quartz plates 4 and 5, there is thus observed a first quartz plate 5, suitable for being positioned above said closures and suitable for being passed through by said first light radiation E1 emitted by said first source of light radiation 9, for the decontamination of the exterior of said closures (see arrow E1—FIG. 3), and a second quartz plate 4, suitable for being positioned below said closures and suitable for being passed through by a second light radiation emitted by the second source of light radiation 9, for the decontamination of the interior of said closures (see arrow I) and, at least partially, for the decontamination of the exterior of the closure (see arrow E2).

The device also includes reflecting tunnels 10 which send the radiation which they reflect back towards the decontamination area 3 through which the closures 2 are passing.

The device illustrated in FIGS. 3 and 4 includes a tubular conduit of rectangular section 12, inside which the decontamination area 3 in which the closures 2 are moving is located.

In the example presented, the conduit 12 extends between the entrance 7 of the decontamination area and the exit 8 of the decontamination area. It must be understood that the conduit 12 could extend beyond the decontamination area, in particular to keep the treated closure in an environment which spares it from being contaminated again.

The conduit 12 thus including two side walls 13 and 14, a top wall 15 and a bottom wall 16.

Each side wall 13 and 14 has a face inside the conduit, each carrying a lateral guide rail 6.

Each top 15 and bottom 16 wall has a window 17 (i.e. a through-opening) of rectangular shape, to which a quartz plate (respectively 5 and 4) is fastened.

The fastening of the quartz plates 4 and 5 to the windows 17 of the walls 16 and 15 is carried out by a tight seal, applied to the exterior of the conduit 12 so as not to disrupt the sliding of the closures 2.

The conduit 12 is therefore totally leakproof.

The advantage of providing a leakproof conduit is to allow the decontamination area to be cleaned, by circulating a cleaning liquid (or steam) inside the conduit 12 without risk of the cleaning liquid (or the steam) coming out of the conduit.

The conduit 12 is preferably made of stainless steel.

Moreover, the conduit 12 makes it possible to protect the decontamination area in the case of breakage of lamps placed outside the conduit.

In fact, perpendicular to the quartz plates 4 and 5 there are positioned two sources for emitting decontaminating radiation 9 (lamps 9), as in the example previously described.

Likewise, the two lamps 9 are surrounded by a reflecting tunnel 10 having a bell-shaped (or curved) section to reflect the emitted radiation and focus it towards the decontamination area.

In the context of the example illustrated in FIGS. 3 and 4, the rails 6 each extend over the entire length of the conduit 12 between the entrance 7 and the exit 8 of the decontamination area 3.

The contact area 61 of the rails is then in contact with the same part of the skirt 20 of the closures 2 during the whole journey of the closures between the entrance 7 and the exit 8 of the decontamination area 3. It is then understood that this contact area 61 cannot be decontaminated in the context of this embodiment. It remains limited, however, because it extends over a contact point of the skirt 20 of a closure 2, the ridge 61 of the lateral guide rail 6 being tangential to the surface of the cylindrical skirt 20.

In order to allow these contact points between the skirt 20 of the closures and the ridge 61 of the rails 6 to be changed, several embodiments can be provided.

Figure 5:
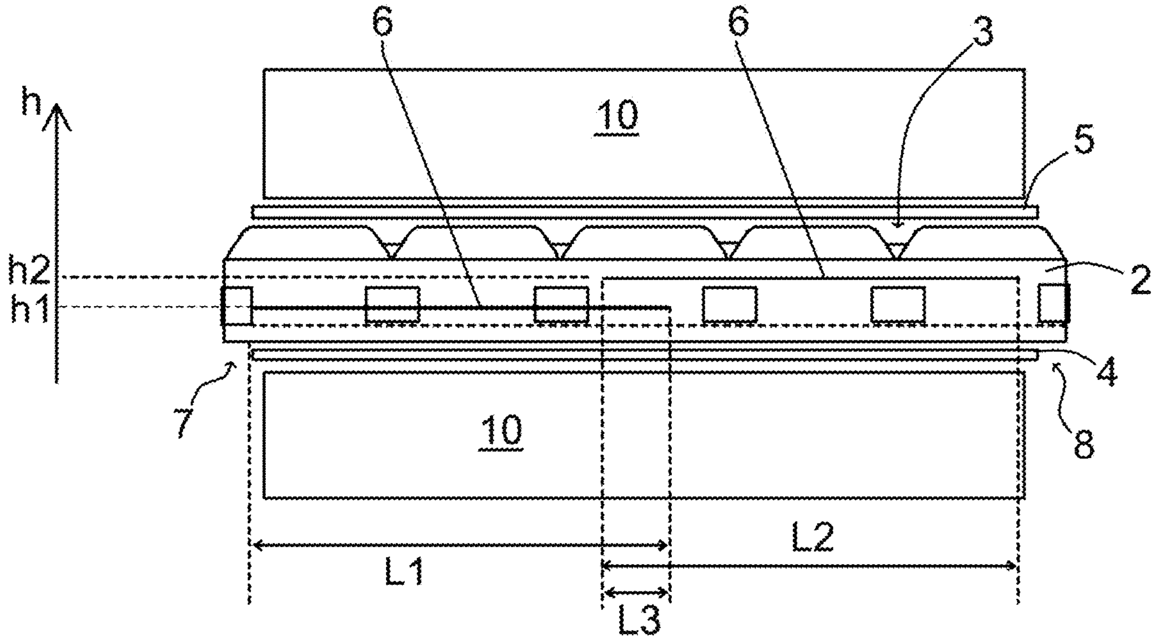
FIG. 5 is a diagrammatic longitudinal sectional view of a device according to a third embodiment of the invention.

The first is shown in FIG. 5 and proposes arranging two rails 6 at different heights h in the decontamination area.

The height h of the decontamination area 3 is delimited between the lower quartz plate 4 and the upper quartz plate 5.

The reflecting tunnels 10 above and below the quartz plates 5 and 4 respectively, as well as five closures 2, "nose to tail", between the entrance 7 of the decontamination area 3 and the exit 8 are also illustrated, diagrammatically.

A first set of guide rails 6 extends at a first height h1 of decontamination area 3 (which corresponds to a first contact height on the skirt 20 of closure 2) over a first length L1 in the decontamination area 3.

A second set of guide rails 6 extends at a second height h2 of decontamination area 3, the height h2 being different from said first height h1, over a second length L2 in the decontamination area, between the entrance 7 and the exit 8 of the decontamination area 3, said second set of guide rails 6 being consecutive and contiguous with the first set of guide rails 6, so that the closures 2 moving in said decontamination area 3 are guided first by said first set of rails at the height h1 then by the second set of rails at the height h2.

In this way, a first contact area of the first set of rails on the closures 2, corresponding to the contact area 61 of the first set of guide rails 6, is decontaminated by the light radiation when the closures 2 move between the rails of the second set of guide rails 6.

It will be noted that the first set of guide rails 6 and the second set of guide rails 6 overlap over a length L3, allowing the closures 2 to pass between the first set of rails and the second set of rails unhindered.

In another embodiment, it could be provided that the two guide rails do not overlap (in which case L3 would be zero).

Thus, the length L1 added to the length L2 is at least equal to, or even greater than, the total length of the decontamination area 3.

In the context of this example, the light radiation emitted is a pulsed radiation.

Figure 6:
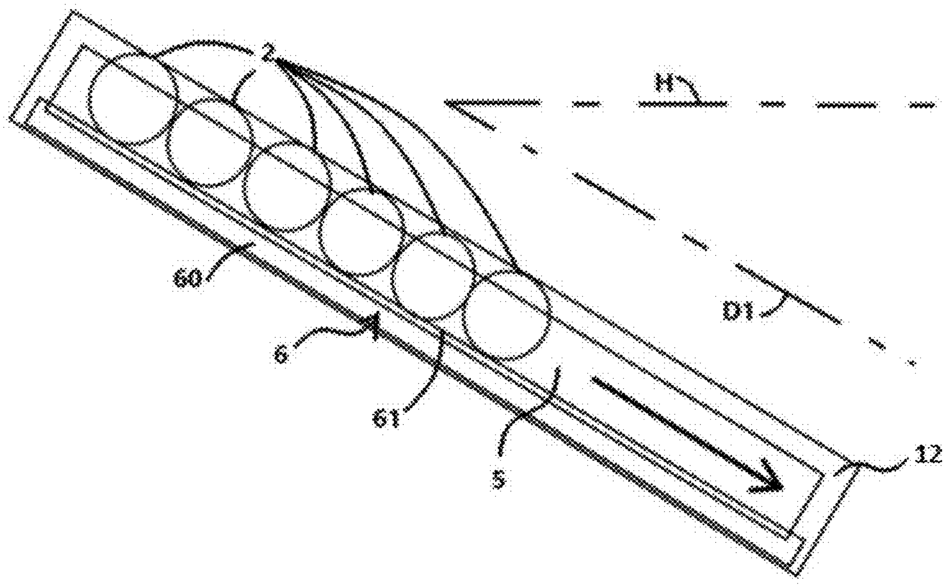
FIG. 6 is a side view of a part of the device according to another embodiment according to the invention, ensuring the displacement of the objects by means of gravity.

Another embodiment, which allows the contact point between the rail and the skirt of the closures to be changed, is illustrated in FIG. 6: the conduit 12 is visible and it is oriented at 90° with respect to the conduit 12 shown in FIG. 5. It will be noted that the conduit 12 is also inclined in a direction D1 with respect to the horizontal H. Thus, the contact area 61 of the rails 6, against which the skirt of the closures rests, is inclined, so that the closures that are in contact with the area 61 move by rolling downwards in the decontamination area. The aim of this embodiment is to generate the rolling motion of the closures about their respective axes: thus the contact area between the closure and the rail changes as the closure advances in the decontamination area. Thus, the whole exterior of the skirt of the closures is decontaminated.

In order to make this possible, the edge (or contact area) 61 of the rail 6 constituting the contact area with the skirt of the closure is produced with a significant roughness or with asperities, to limit the sliding of the closures on the rail in order to cause them to rotate. By providing an angle of inclination of the conduit 12 of less than or equal to 30°, or substantially less than or equal to 30°, the result is that the pressure between two closures 2 is sufficiently low that the friction of the contact area 61 of the rail prevails over the friction between two closures and that the closures roll on the area 61 of the rail 6.

According to yet another variant which allows the contact point between the rail 6 and the skirt of the closure to be changed between the entrance and the exit of the decontamination area, there could be provided a horizontal conduit and rails 6 the contact area 61 of which is oriented in a direction which is inclined with respect to the horizontal between the entrance 7 and the exit 8 of the decontamination area (embodiment not illustrated).

In the context of this embodiment, a decontaminating radiation that is emitted continuously can be provided. In such a case, the position of the contact of the rail varies over the height of the closure as the closure advances in the decontamination area. This embodiment would be compatible with continuous emitters of decontaminating radiation of the mercury lamp, LED, excimer etc. type.

In the context of the examples presented above, it will be noted that the lamp 9 (or source for emitting a decontaminating light radiation) extends over a length which is substantially equal to the length of decontamination area between the entrance 7 of the decontamination area and the exit 8 of the decontamination area.

In the examples presented, it will also be noted that the guide rails 6 extend in a linear direction which is straight.

In the context of another embodiment, and without exceeding the scope of the invention, it could be provided that the lateral guide rails each extend in a non-linear direction (i.e. a direction which is not straight, i.e. a curve), to generate a lateral displacement of the closures moving in said decontamination area (embodiment not illustrated).

Figure 7:
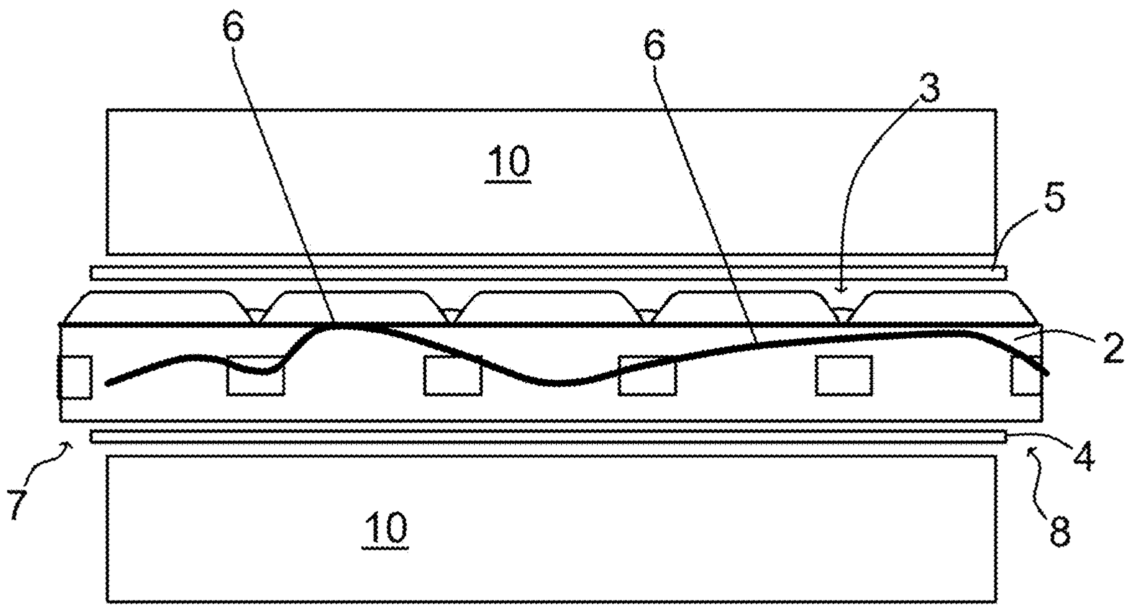
FIG. 7 is a diagrammatic longitudinal sectional view of a device according to another embodiment of the invention.

According to another embodiment variant, the device shown in FIG. 7 provides at least one lateral rail 6 which extends in a non-linear (curved) direction, so that the closure (or more generally the object) to be decontaminated comes into contact with the rail at different locations as it advances in the decontamination area, between the entrance and the exit. Although it is non-linear (curved), the direction of the lateral rail extends in a substantially vertical plane (or according to a first plane orientation), this plane being a plane parallel to the longitudinal axis of the device so that the closures always advance in a straight linear direction between the entrance and the exit of the decontamination area 3.

In other words, although the rail extends in a curved direction, the direction which the closures follow is straight.

It is also provided to circulate air in the decontamination area 3, in particular to limit the temperature increase in the decontamination area.

The direction of circulation of the air is opposite with respect to the direction of movement of the closures 2 in the decontamination area 3.

It can also be provided to circulate air in the reflecting tunnels 10 surrounding the lamps 9, to cool the two spaces in the vicinity of the lamps 9, between the quartz plates 4 and 5 and the walls of the reflecting tunnels 10.

It is understood from the preceding how the invention makes it possible to propose a device which decontaminates both the interior and the exterior of the closures in an efficient manner by limiting the contacts between the closures and the guide rails, and by reflecting the decontaminating light radiation close to the contact between the guide rail and the closures.

However, it must be understood that the invention is not limited specifically to the embodiments illustrated and previously described and that it extends to the utilization of any equivalent means.

For example, the lamps utilized as sources for emitting decontaminating light radiation could be different: different lamps could be utilized [without] exceeding the scope of the invention. For example, low-pressure lamps or LEDs (low-power emitter) could be utilized with plates made of transparent plastic material replacing quartz plates.

Other pieces of equipment could also be provided in the device according to the invention: for example, the device could be equipped with a system for detecting breakage of quartz.

The invention claimed is:

1. A device for decontaminating objects, including:

a decontamination area in which the objects move by means of gravity between a decontamination area entrance and a decontamination area exit, at least one source for emitting a light radiation into the decontamination area, said light radiation being suitable for decontaminating said objects moving in said area;

a conduit which extends between the decontamination area entrance and the decontamination area exit;

a device for positioning the objects in said decontamination area, to position the objects in a predetermined arrangement, including at least two elements for guiding said objects;

said at least two elements for guiding said objects include at least one lateral rail included into said conduit and on which said objects are at least partially guided, said at least one lateral rail comprising a contact area with at least one object and at least one reflective area which is contiguous with said contact area and which is suitable for reflecting said light radiation onto said at least one object, said reflective area being constituted by a face of said at least one lateral guide rail; and said at least one lateral guide rail has a V-shaped profile, comprising two contiguous faces, at least one of the two faces being suitable for reflecting said light radiation and constituting said at least one reflective area, the two faces extending on either side of a ridge, said contact area of said at least one lateral rail being constituted only by the ridge.

2. The device for decontaminating objects according to claim 1, characterized in that said contact area of said at least one lateral rail is situated at at least two different locations in said decontamination area, including a first location in said decontamination area in which the contact area of said at least one rail touches at least one of said objects at a first contact point, line or surface but not at a second contact point, line or surface and a second location in said decontamination area in which the contact area of said at least one rail touches the same object at the second contact point, line or surface but not at the first contact point, line or surface, said second contact point, line or surface on said object being different from said first contact point, line or surface.

3. The device for decontaminating objects according to claim 2, further including a control device of the source for emitting the light radiation at least one of arranged and programmed to emit said light radiation in the form of a plurality of flashes of light, in the first location in said decontamination area then in the second location in said decontamination area, a first flash of light of said plurality of flashes of light emitted in said first location being distinct from a second flash of light of said plurality of flashes of light emitted in the second location.

4. The device for decontaminating objects according to claim 1, characterized in that with said at least one object moving in said decontamination area, said contact area being linear and straight.

5. The device for decontaminating objects according to claim 1, characterized in that said at least one lateral rail is made of metal.

6. The device for decontaminating objects according to claim 1, characterized in that said at least one reflective area has a roughness of less than 0.2 μm.

7. The device for decontaminating objects according to claim 1, further including a circuit for cooling the decontamination area, to keep said positioning device at a temperature below a predetermined temperature when the decontamination area receives said light radiation, said cooling circuit being integrated into said positioning device at least partially in said at least one lateral rail.

8. The device for decontaminating objects according to claim 1, characterized in that said guide elements include at least one plate, said plate being positioned above or below the objects and suitable for being passed through by said light radiation emitted by said at least one source for emitting light radiation.

9. The device for decontaminating objects according to claim 1, further including a first source for emitting a first light radiation and a second source for emitting a second light radiation, and in that the guide elements include two plates suitable for allowing a light radiation to pass through making it possible to decontaminate said objects, one of the two plates being positioned above said objects and suitable for being passed through by said first light radiation emitted by said first source of light radiation, for the decontamination of the exterior of said objects, and the other plate being positioned below said objects and suitable for being passed through by said second light radiation emitted by said second source of light radiation, for the decontamination of the interior and at least partially the exterior of said objects.

10. The device according to claim 1, characterized in that said at least one source for emitting light radiation is a source for emitting pulsed light.

11. The device according to claim 1, characterized in that said at least one source for emitting light radiation is combined with a reflector, to focus said light radiation emitted by said at least one source onto the objects in said decontamination area.

12. The device according to claim 1, characterized in that the light radiation emitted by said at least one emission source is an ultraviolet radiation the wavelength of which is preferably comprised substantially between 200 and 300 nm.

13. The device according to claim 1, further including said conduit including said at least one lateral rail on which the objects are at least partially guided and including at least a first wall having at least a first window receiving a first plate, suitable for allowing a light radiation to pass through making it possible to decontaminate said objects, said first window extending substantially from a first end of the conduit to substantially a second end of the conduit under said source for emitting light radiation, said conduit being leakproof to allow it to be cleaned.

14. The device according to claim 13, characterized in that said conduit includes a second wall, opposite said first wall, said second wall having at least a second window receiving a second plate suitable for allowing a light radiation to pass through making it possible to decontaminate said objects, said second window extending substantially from a first end of the conduit to substantially a second end of the conduit under a second source for emitting light radiation.

15. The device according to claim 1, further including a first set of two guide rails which extends at a first height and over a first length of decontamination area between said entrance and said exit of decontamination area, and a second set of two guide rails which extends at a second height, different from said first height, and over a second length of decontamination area, said second set of guide rails being consecutive and contiguous with the first set of guide rails so that the objects moving in said decontamination area are guided first by said first set of rails then by the second set of guide rails and so that a first contact area on the objects moving between the guide rails of the first set and corresponding to the contact area of the first set of guide rails is decontaminated by the light radiation when the objects move between the guide rails of the second set of guide rails.

16. The device according to claim 1, further including two lateral rails, each extending in a curved direction, to generate a lateral displacement of the objects moving in said decontamination area.

17. The device according to claim 1, characterized in that said at least one lateral rail extends in a curved direction and generating a straight linear displacement of the objects in said decontamination area without lateral displacement.

18. A method for decontaminating objects utilizing a device according to claim 1, said method ensuring:

the movement by means of gravity of objects in the decontamination area between said entrance of said decontamination area and said exit of said decontamination area, said objects being guided in a predetermined position by at least two guide elements of a positioning device;

the decontamination of said objects moving in said area by emitting a light radiation into the decontamination area;

the decontamination of said objects is carried out at least partially by the reflection of said light radiation onto said at least one object on at least one reflective area of at least one lateral rail which said at least two guide elements (4-6) include, and the movement of said objects is carried out by contact of said objects on a contact area of said at least one lateral rail, said contact area being contiguous with said reflective area of said at least one lateral rail, said reflective area being constituted by a face of said at least one lateral guide rail, and said at least one lateral guide rail has a V-shaped profile, comprising two contiguous faces, at least one of the two faces being suitable for reflecting said light radiation and constituting said at least one reflective area, the two faces extending on either side of a ridge, said contact area of said at least one lateral rail being constituted only by the ridge.

* * * * *